(12) United States Patent
Westland et al.

(10) Patent No.: US 6,300,259 B1
(45) Date of Patent: Oct. 9, 2001

(54) CROSSLINKABLE CELLULOSIC FIBROUS PRODUCT

(75) Inventors: John A. Westland, Auburn; Colin Elston, Gig Harbor, both of WA (US)

(73) Assignee: Weyerhaeuser Company, Federal Way, WA (US)

( * ) Notice: Subject to any disclaimer, the term of this patent is extended or adjusted under 35 U.S.C. 154(b) by 0 days.

(21) Appl. No.: 09/299,712

(22) Filed: Apr. 26, 1999

(51) Int. Cl.[7] .................................................. B32B 9/04
(52) U.S. Cl. ........................ 442/153; 442/59; 442/118; 442/160; 442/165
(58) Field of Search ......................... 442/59, 153, 160, 442/165, 118

(56) References Cited

U.S. PATENT DOCUMENTS

| | | | |
|---|---|---|---|
| 4,624,890 | * 11/1986 | Lloyd et al. | 428/290 |
| 5,071,681 | * 12/1991 | Manning et al. | 427/392 |
| 5,149,334 | * 9/1992 | Lahrman et al. | 604/367 |
| 5,183,707 | * 2/1993 | Herron et al. | 428/364 |
| 5,789,326 | * 8/1998 | Hansen et al. | 442/59 |
| 5,938,995 | 8/1999 | Koltisko, Jr. et al. . | |

FOREIGN PATENT DOCUMENTS

| | | | |
|---|---|---|---|
| 0251674A2 | * | 1/1988 | (EP) . |
| 0427317A2 | * | 5/1991 | (EP) . |
| WO 96/17573 | * | 6/1996 | (WO) . |

* cited by examiner

*Primary Examiner*—Elizabeth M. Cole
*Assistant Examiner*—Norca L. Torres
(74) *Attorney, Agent, or Firm*—Christensen O'Connor Johnson Kindness PLLC

(57) ABSTRACT

A crosslinkable cellulosic fibrous product that includes cellulosic fibers and a crosslinking agent is disclosed. The crosslinkable cellulosic fibrous product can be formed as a web or sheet that has structural integrity and sheet strength sufficient to permit the fibrous web to be rolled, transported, and used in rolled form in subsequent processes. The crosslinkable fibrous product can be converted into a crosslinked fibrous product by subjecting the product to conditions sufficient to effect intrafiber crosslinking. Alternatively, the web can be fiberized and the resulting individual crosslinkable fibers combined with other fibers and/or other materials to provide a fibrous web containing crosslinkable cellulosic fibers. Subjecting such a web to crosslinking conditions provides a fibrous web that includes, in addition to other fibers or materials, crosslinked cellulosic fibers.

10 Claims, No Drawings

CROSSLINKABLE CELLULOSIC FIBROUS PRODUCT

FIELD OF THE INVENTION

The present invention relates generally to a cellulosic fibrous product and, more particularly, to a crosslinkable cellulosic fibrous product that includes cellulosic fibers and a crosslinking agent.

BACKGROUND OF THE INVENTION

Crosslinked cellulosic fibers are advantageously incorporated into a variety of fibrous products to enhance product bulk and resilience. Absorbent articles, such as diapers, are typically formed from fibrous composites that include, in addition to crosslinked cellulosic fibers, absorbent fibers such as wood pulp fibers. When incorporated into absorbent articles, such fibrous composites can provide a product that offers the advantages of high liquid acquisition rate and high liquid wicking capacity imparted by the crosslinked fibers and the absorbent fibers, respectively. However, fibrous composites that include relatively high percentages of crosslinked fibers suffer from low sheet strength.

The relatively low strength of sheets that include crosslinked fibers is due to the loss of hydrogen bonding sites that accompanies cellulose crosslinking. As a result of their chemical modification, crosslinked cellulosic fibers lack hydroxyl groups that are necessary for forming hydrogen bonds between fibers. The inability of crosslinked fibers to form interfiber bonds generally precludes their formation into sheets or webs having any significant structural integrity. Thus, unlike other cellulosic fibrous materials that can be formed into sheets or webs and then transported as rolled goods to a customer for further processing or use, crosslinked fibers are generally transported as bales.

Furthermore, in contrast to other cellulosic fibrous products that can be readily produced, transported, and used in processes as rolled goods, the handling and use of crosslinked cellulosic fibrous bales can be difficult and costly. For example, bale opening equipment is expensive. In addition, fibrous bale handling often results in the creation of dust, a potential health hazard.

Accordingly, there exists a need for a crosslinked cellulosic fibrous product that can be readily formed, transported, and used in subsequent processes. Alternatively, there is a need for a readily formed and transported cellulosic fibrous product that can be converted to a useful crosslinked cellulosic fibrous product on arrival at the processing site. Such a fibrous product is ideally converted to a crosslinked cellulosic product without the need for expensive equipment and/or additional time-consuming processing. The present invention seeks to fulfill these needs and provides further related advantages.

SUMMARY OF THE INVENTION

In one aspect, the present invention provides a crosslinkable cellulosic fibrous product that includes cellulosic fibers and a crosslinking agent.

In another aspect of the invention, a method for forming a crosslinkable cellulosic fibrous product is provided.

In a further aspect, the present invention provides methods for using the crosslinkable cellulosic fibrous product.

DETAILED DESCRIPTION OF THE PREFERRED EMBODIMENT

The fibrous product of the present invention is a crosslinkable cellulosic fibrous product that includes cellulosic fibers and a crosslinking agent. The crosslinkable cellulosic fibrous product can be formed as a web or sheet that has structural integrity and sheet strength sufficient to permit the fibrous web to be rolled, transported, and used in rolled form in subsequent processes. As used herein, the term "crosslinkable" refers to a fibrous cellulosic web that has been treated with a crosslinking agent, but has not been subjected to conditions sufficient to effect substantial cellulose crosslinking.

The crosslinkable product of the invention includes cellulosic fibers to which a crosslinking agent has been applied. Generally, any cellulosic fiber that can be formed into a fibrous web and crosslinked is suitable. Similarly, suitable crosslinking agents include any agent that crosslinks cellulose at elevated temperature. The crosslinkable product can be prepared by applying a crosslinking agent to a cellulosic fibrous web and then drying the treated web without curing the crosslinking agent. The resulting product is a dried fibrous web, preferably in an extended sheet form, that can be rolled, transported, and stored until use.

The crosslinkable fibrous product can be converted into a crosslinked fibrous product by subjecting the product to conditions sufficient to effect intrafiber crosslinking by, for example, heating to a temperature to cure the crosslinking agent. The fibrous web can be heated at about the crosslinking agent's cure temperature to provide a web that includes crosslinked fibers. Alternatively, the web can be fiberized, for example, at a manufacturing site remote from initial web formation, and the resulting individual crosslinkable fibers can be combined with other fibers (e.g., hemp, bagasse, cotton, groundwood, bleached and unbleached pulp, recycled or secondary fibers) and/or other materials (e.g., superabsorbent particles and wet strength agents) to provide a fibrous web containing crosslinkable cellulosic fibers. Subjecting such a web to crosslinking conditions (e.g., heating at about the cure temperature) provides a fibrous web that includes, in addition to other fibers or materials, crosslinked cellulosic fibers. Thus, the crosslinkable product of the invention allows for the formation of crosslinked fibrous products at a site remote from crosslinkable product formation without having to apply crosslinking agent at the site of ultimate web formation. The crosslinkable product further offers the advantage of convenience associated with transport to and use at the remote site by virtue of its form as a rolled product.

Cellulosic fibers are a principal component of the crosslinkable fibrous product of this invention. Suitable fibers for forming the product of the invention are known to those skilled in the art and include any fiber or fibrous mixture that can be crosslinked and from which a fibrous web or sheet can be formed.

Although available from other sources, cellulosic fibers are derived primarily from wood pulp. Suitable wood pulp fibers for use with the invention can be obtained from well-known chemical processes such as the kraft and sulfite processes, with or without subsequent bleaching. Pulp fibers can also be processed by thermomechanical, chemithermomechanical methods, or combinations thereof The preferred pulp fiber is produced by chemical methods. Groundwood fibers, recycled or secondary wood pulp fibers, and bleached and unbleached wood pulp fibers can be used. Softwoods and hardwoods can be used. Details of the selection of wood pulp fibers are well known to those skilled in the art. These fibers are commercially available from a number of companies, including Weyerhaeuser Company, the assignee of the present invention. For example, suitable cellulose fibers produced from southern pine that are usable with the present invention are available from Weyerhaeuser Company under the designations CF416, NF405, PL416, FR516, and NB416.

The wood pulp fibers useful in the present invention can also be pretreated prior to use. This pretreatment may include physical treatment, such as subjecting the fibers to steam, or chemical treatment.

Although not to be construed as a limitation, examples of pretreating fibers include the application of surfactants or other liquids, which modify the surface chemistry of the fibers. Other pretreatments include incorporation of antimicrobials, pigments, dyes and densification or softening agents. Fibers pretreated with other chemicals, such as thermoplastic and thermosetting resins also may be used. Combinations of pretreatments also may be employed. Similar treatments can also be applied after formation of the fibrous product in post-treatment processes.

Cellulosic fibers treated with particle binders and/or densification/softness aids known in the art can also be employed in accordance with the present invention. The particle binders serve to attach other materials, such as superabsorbent polymers, as well as others, to the cellulosic fibers. Cellulosic fibers treated with suitable particle binders and/or densification/softness aids and the process for combining them with cellulose fibers are disclosed in the following U.S. patents: (1) U.S. Pat. No. 5,543,215, entitled "Polymeric Binders for Binding Particles to Fibers"; (2) U.S. Pat. No. 5,538,783, entitled "Non-Polymeric Organic Binders for Binding Particles to Fibers"; (3) U.S. Pat. No. 5,300,192, entitled "Wet Laid Fiber Sheet Manufacturing With Reactivatable Binders for Binding Particles to Binders"; (4) U.S. Pat. No. 5,352,480, entitled "Method for Binding Particles to Fibers Using Reactivatable Binders"; (5) U.S. Pat. No. 5,308,896, entitled "Particle Binders for High-Bulk Fibers"; (6) U.S. Pat. No. 5,589,256, entitled "Particle Binders that Enhance Fiber Densification"; (7) U.S. Pat. No. 5,672,418, entitled "Particle Binders"; (8) U.S. Pat. No. 5,607,759, entitled "Particle Binding to Fibers"; (9) U.S. Pat. No. 5,693,411, entitled "Binders for Binding Water Soluble Particles to Fibers"; (10) U.S. Pat. No. 5,547,745, entitled "Particle Binders"; (11) U.S. Pat. No. 5,641,561, entitled "Particle Binding to Fibers"; (12) U.S. Pat. No. 5,308,896, entitled "Particle Binders for High-Bulk Fibers"; (13) U.S. Pat. No. 5,498,478, entitled "Polyethylene Glycol as a Binder Material for Fibers"; (14) U.S. Pat. No. 5,609,727, entitled "Fibrous Product for Binding Particles"; (15) U.S. Pat. No. 5,571,618, entitled "Reactivatable Binders for Binding Particles to Fibers"; (16) U.S. Pat. No. 5,447,977, entitled "Particle Binders for High Bulk Fibers"; (17) U.S. Pat. No. 5,614,570, entitled "Absorbent Articles Containing Binder Carrying High Bulk Fibers; (18) U.S. Pat. No. 5,789,326, entitled "Binder Treated Fibers"; and (19) U.S. Pat. No. 5,611,885, entitled "Particle Binders", each expressly incorporated herein by reference.

In addition to natural fibers, synthetic fibers including polymeric fibers, such as polyolefin, polyamide, polyester, polyvinyl alcohol, polyvinyl acetate fibers, can also be incorporated into the crosslinkable fibrous product. Suitable synthetic fibers include, for example, polyethylene terephthalate, polyethylene, polypropylene, nylon, and rayon fibers. Other suitable synthetic fibers include those made from thermoplastic polymers, cellulosic and other fibers coated with thermoplastic polymers, and multicomponent fibers in which at least one of the components includes a thermoplastic polymer. Single and multicomponent fibers can be manufactured from polyester, polyethylene, polypropylene, and other conventional thermoplastic fibrous materials. Single and multicomponent fibers are commercially available. Suitable bicomponent fibers include Celbond® fibers available from Hoechst-Celanese Company. The fibrous product can also include combinations of natural and synthetic fibers.

The fibrous product of the present invention includes a crosslinking agent. The crosslinking agent useful in the present invention is a latent crosslinking agent in that, although the crosslinking agent is applied to a web of cellulose fibers and the resulting treated fibers dried to provide the crosslinkable product, no significant crosslinking occurs during the product's formation process and the resulting product is substantially free from crosslinks, particularly interfiber crosslinks. This enables the sheet to be readily defibered, e.g., in a hammermill, without excessive energy requirements and the production of dust and knots normally associated with defibration of crosslinked webs. Suitable crosslinking agents useful in the invention do not crosslink cellulose to any significant degree under the conditions for forming the crosslinkable product.

Crosslinking typically requires heating treated fibers at a temperature and for a time sufficient to cure the crosslinking agent. By avoiding subjecting treated cellulosic fibers to elevated temperature, crosslinking can be prevented. Thus, in one embodiment of the present invention, suitable crosslinking agents include those that do not undergo crosslinking at temperatures below the highest temperature (i.e., drying temperature) of the product's formation process (i.e., the formation process does not reach the cure temperature of the crosslinking agent).

Alternatively, because the crosslinking reaction is typically pH dependent, the crosslinking agent can be applied to the cellulosic fibers at a pH at which no crosslinking can occur. Generally, crosslinking optimally occurs in the pH range from about 2 to about 4. Application of the crosslinking agent at a pH outside of the crosslinking pH range will substantially prevent crosslinking. As with the optimal pH for crosslinking, the actual pH for preventing the crosslinking reaction will depend on the particular crosslinking agent and the formation conditions employed.

For crosslinking agents that undergo crosslinking in the presence of a catalyst, application of the crosslinking agent without the catalyst can also provide a crosslinkable product that is substantially free from crosslinks.

Suitable cellulose crosslinking agents include crosslinking agents known in the art such as aldehyde and urea-based formaldehyde addition products. See, for example, U.S. Pat. Nos. 3,224,926; 3,241,533; 3,932,209; 4,035,147; 3,756,913; 4,689,118; 4,822,453; U.S. Pat. No. 3,440,135, issued to Chang; U.S. Pat. No. 4,935,022, issued to Lash et al.; U.S. Pat. No. 4,889,595, issued to Herron et al.; U.S. Pat. No. 3,819,470, issued to Shaw et al.; U.S. Pat. No. 3,658,613, issued to Steiger et al.; and U.S. Pat. No. 4,853,086, issued to Graef et al., all of which are expressly incorporated herein by reference in their entirety. Other suitable crosslinking agents include carboxylic acid crosslinking agents such as polycarboxylic acids. U.S. Pat. Nos. 5,137,537; 5,183,707; and 5,190,563, describe the use of $C_2$–$C_9$ polycarboxylic acids that contain at least three carboxyl groups (e.g., citric acid and oxydisuccinic acid) as crosslinking agents.

Suitable urea-based crosslinking agents include substituted ureas such as methylolated ureas, methylolated cyclic ureas, methylolated lower alkyl cyclic ureas, methylolated dihydroxy cyclic ureas, dihydroxy cyclic ureas, and lower alkyl substituted cyclic ureas. Specific preferred urea-based crosslinking agents include dimethyldihydroxy urea (DMDHU, 1,3-dimethyl-4,5-dihydroxy-2-imidazolidinone), dimethyloldihydroxyethylene urea (DMDHEU, 1,3-dihydroxymethyl-4,5-dihydroxy-2-imidazolidinone), dimethylol urea (DMU, bis[N-hydroxymethyl]urea), dihydroxyethylene urea (DHEU, 4,5-dihydroxy-2-imidazolidinone), dimethylolethylene urea (DMEU, 1,3-dihydroxymethyl-2-imidazolidinone), and dimethyldihydroxyethylene urea (DDI, 4,5-dihydroxy-1,3-dimethyl-2-imidazolidinone). Other suitable substituted ureas include glyoxal adducts of ureas.

Suitable polycarboxylic acid crosslinking agents include citric acid, tartaric acid, malic acid, succinic acid, glutaric acid, citraconic acid, itaconic acid, tartrate monosuccinic acid, and maleic acid. Other polycarboxylic acid crosslinking agents include polymeric polycarboxylic acids such as poly(acrylic acid), poly(methacrylic acid), poly(maleic acid), poly(methylvinylether-co-maleate) copolymer, poly(methylvinylether-co-itaconate) copolymer, copolymers of acrylic acid, and copolymers of maleic acid. The use of polymeric polycarboxylic acid crosslinking agents such as polyacrylic acid polymers, polymaleic acid polymers, copolymers of acrylic acid, and copolymers of maleic acid is described in U.S. patent application Ser. No. 08/989,697, filed Dec. 12, 1997, and assigned to Weyerhaeuser Company. Mixtures or blends of crosslinking agents can also be used.

In a preferred embodiment, the crosslinking agent is a substituted urea.

The crosslinking agent is present in the fibrous product in an amount from about 1 to about 10 percent by weight, and preferably from about 4 to about 6 percent by weight, based on the total weight of the fibrous product.

In another aspect, the present invention provides a method for forming a crosslinkable cellulosic fibrous product. The crosslinkable product is formed by applying a crosslinking agent to a mat of cellulosic fibers and then drying the treated mat such that substantially no crosslinking occurs and the product is substantially free from crosslinks. The cellulosic fibrous mat can be laid using conventional papermaking methods and devices. Once laid, the fibrous mat is then treated with a crosslinking agent. The crosslinking agent can be applied as a solution to one or both surfaces of the mat using any one of a variety of methods known in the art including, for example, spraying, rolling, and dipping. Cellulosic fibers in the treated mat are coated and/or impregnated with the crosslinking agent. After the crosslinking agent has been applied, the treated mat is then dried without heating to a temperature sufficient to cure the crosslinking agent.

The cellulosic web formed in accordance with the present invention can be an extended sheet having sheet strength sufficient to permit the sheet to be formed into a rolled product. Thus, in one embodiment, the present invention provides a crosslinkable fibrous product in the form of a rolled good that is readily transported, stored, and used.

The product of the invention can be a source for crosslinked cellulosic fibers and, as such, can be used as a raw material for processes that incorporate crosslinked fibers into a variety of fibrous products. Thus, in a further aspect, the present invention provides a method for using the crosslinkable product described above.

In one method, the crosslinkable product is separated into individualized fibers, at least a portion of which are coated and/or impregnated with a crosslinking agent. The individualized fibers are then incorporated into a fibrous web and further processed by, for example, combining with additional fibers or materials and/or subjecting the fibrous web to further chemical treatments. Ultimately, the fibrous web that includes fibers from the crosslinkable product is then subjected to conditions (e.g., application of heat, catalyst, or pH adjustment) sufficient to cure the crosslinking agent and to provide a crosslinked product.

The crosslinkable product of the present invention can be supplied in a fibrous rolled form and readily incorporated into subsequent processes. For example, the crosslinkable product can be readily separated into individual fibers by fiberization.

The rolled form of the crosslinkable product can be continuously introduced into a fiberizer to provide individualized fibers that are coated/impregnated with crosslinking agent. These individualized fibers can be formed into a fibrous web by, for example, air or wet laying the fibers onto a foraminous support (e.g., forming wire). These individualized fibers can be combined with additional fibers (e.g., other cellulosic fibers such as wood pulp fibers and/or synthetic fibers) prior to or after laying. The fibers can also be combined with other materials including wet-strength agents, particle binders, or particles such as absorbent particles (e.g., superabsorbent polymers).

Once deposited, the crosslinkable fibers can be further chemically treated to, for example, effect crosslinking. For example, the fibrous web can be heated at a temperature and for a time sufficient to cure the crosslinking agent and to provide a crosslinked fibrous product. Another method for effecting crosslinking in a web that includes fibers from the crosslinkable product is to treat the fibrous web with a crosslinking catalyst and then heating the resulting web to cure the crosslinking agent. Suitable crosslinking catalysts, known to those in the art, accelerate the bonding reaction between the crosslinking agent and cellulose fiber. Catalysts can include acidic salts, such as ammonium chloride, ammonium sulfate, aluminum chloride, magnesium chloride, magnesium nitrate, and alkali metal salts of phosphorous-containing acids. In a preferred embodiment, the crosslinking catalyst is sodium hypophosphite.

Another method for crosslinking a web that includes fibers from the crosslinkable product involves adjusting the pH of the web to facilitate the crosslinking reaction. For example, a solution can be applied to wet the web and to bring the pH into a range such that the crosslinking reaction will occur on heating (e.g., adjust to about pH 2–4 with aqueous acid).

Other chemical treatments include those known in pulp and papermaking methods. For example, the hydrophilicity of the fibers or the tensile strength of the web can be modified by chemical treatment. To increase the strength of the resulting crosslinked fibrous web, a wet-strength agent can be applied to the web, preferably prior to curing and crosslinking. Suitable wet-strength agents include cationic modified starch having nitrogen-containing groups (e.g., amino groups) such as those available from National Starch and Chemical Corp., Bridgewater, N.J.; latex; wet-strength resins such as polyamide-epichlorohydrin resin (e.g., Kymene® 557LX, Hercules, Inc., Wilmington, Del.), polyacrylamide resin (described, for example, in U.S. Pat. No. 3,556,932 issued Jan. 19, 1971 to Coscia et al.; also, for example, the commercially available polyacrylamide marketed by American Cyanamid Co., Stanford, Conn., under the trade name Parez™ 631 NC); urea formaldehyde and melamine formaldehyde resins, and polyethylenimine resins. A general discussion on wet-strength resins utilized in the paper field, and generally applicable in the present invention, can be found in TAPPI monograph series No. 29, "Wet Strength in Paper and Paperboard", Technical Association of the Pulp and Paper Industry (New York, 1965).

The crosslinkable cellulosic fibrous product of the present invention can be utilized to prepare crosslinked cellulosic fibrous products that can be advantageously incorporated into a variety of absorbent articles, such as diapers, including disposable diapers and training pants; feminine care products, including sanitary napkins, tampons, and pant liners; adult incontinence products; toweling; surgical and dental sponges; bandages; food tray pads; and the like.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A crosslinkable fibrous product comprising cellulosic fibers and a crosslinking agent, wherein the product comprises substantially noncrosslinked fibers, and wherein the product is a rolled sheet.

2. The product of claim 1 wherein the crosslinking agent is present in an amount from about 1 to about 10 cent by weight based on the total weight of the product.

3. The product of claim 1 wherein the crosslinking agent is present in an amount from about 4 to about 6 percent by weight based on the total weight of the product.

4. The product of claim 1 wherein the crosslinking agent is selected from the group consisting of substituted ureas, polycafboxylic acids, and glyoxal adducts of ureas.

5. The product of claim 1 further comprising a particle binder.

6. The product of claim 1 further comprising a wet-strength agent.

7. The product of claim 1 wherein the wet-strength agent comprises a polyamide-epichlorohydrin resin.

8. The product of claim 1 wherein the wet-strength agent comprises a polyacrylamide resin.

9. The product of claim 1 wherein the wet-strength agent comprises a latex.

10. A crosslinkable fibrous product comprising cellulosic fibers treated with a crosslinking agent and a wet-strength agent, wherein the product comprises substantially non-crosslinked fibers, and wherein the product is a rolled sheet.

* * * * *